United States Patent
Sylla et al.

(10) Patent No.: US 9,642,233 B2
(45) Date of Patent: May 2, 2017

(54) METHOD AND ARRANGEMENT FOR GENERATING A JET OF FLUID, METHOD AND SYSTEM FOR TRANSFORMING THE JET INTO A PLASMA, AND USES OF SAID SYSTEM

(75) Inventors: Soriba Franciszek (François) Sylla, Cachan (FR); Victor Armand Malka, Paris (FR); Alessandro Federico Flacco, Paris (FR); Mina Ivanova Veltcheva, Paris (FR); Subhendu Kahaly, Villebon-sur-Yvette (FR)

(73) Assignee: ECOLE POLYTECHNIQUE, Palaiseau (FR)

( * ) Notice: Subject to any disclaimer, the term of this patent is extended or adjusted under 35 U.S.C. 154(b) by 446 days.

(21) Appl. No.: 14/123,791

(22) PCT Filed: Jun. 8, 2012

(86) PCT No.: PCT/FR2012/051297
§ 371 (c)(1),
(2), (4) Date: May 28, 2014

(87) PCT Pub. No.: WO2012/168670
PCT Pub. Date: Dec. 13, 2012

(65) Prior Publication Data
US 2014/0254766 A1    Sep. 11, 2014

(30) Foreign Application Priority Data
Jun. 9, 2011   (FR) ...................................... 11 55056

(51) Int. Cl.
*H05G 2/00* (2006.01)
*H05H 1/54* (2006.01)
(Continued)

(52) U.S. Cl.
CPC ....... *H05G 2/006* (2013.01); *H01J 37/32009* (2013.01); *H01J 37/32669* (2013.01);
(Continued)

(58) Field of Classification Search
CPC ... A61B 6/00; A61B 6/40; H05G 2/00; H05G 2/001; H05G 2/003; H05G 2/006;
(Continued)

(56) References Cited

U.S. PATENT DOCUMENTS

| 4,589,123 A | 5/1986 | Pearlman et al. |
| 5,577,092 A | 11/1996 | Kublak et al. |

(Continued)

FOREIGN PATENT DOCUMENTS

| DE | 195 03 549 C1 | 6/1996 |
| KR | 20-2010-0012708 U | 12/2010 |
| WO | WO 2010/086241 A1 | 8/2010 |

OTHER PUBLICATIONS

Smith, R., et al., "Characterization of a cryogenically cooled high-pressure gas jet for laser/cluster interaction experiments", Nov. 1998, Review of Scientific Instruments, vol. 69, No. 11, pp. 3798-3804.*

(Continued)

*Primary Examiner* — Anastasia Midkiff
(74) *Attorney, Agent, or Firm* — Leydig, Voit & Mayer, Ltd.

(57) ABSTRACT

A method and apparatus for generating a pulsed jet of fluid, and transforming the jet into a plasma. The method includes using a high-pressure rapid solenoid valve, and a pipe mounted on an outlet opening of the solenoid valve to produce a pulsed fluid jet which is sub-millimetric in size, and the atomic density of which is more than $10^{20}$ cm$^{-3}$.

23 Claims, 5 Drawing Sheets

(51) Int. Cl.
*H01J 37/32* (2006.01)
*A61B 6/00* (2006.01)
*H05H 1/22* (2006.01)

(52) U.S. Cl.
CPC ............. *H05G 2/001* (2013.01); *H05G 2/003* (2013.01); *H05G 2/008* (2013.01); *H05H 1/54* (2013.01); *A61B 6/40* (2013.01); *H01J 2237/152* (2013.01); *H01J 2893/0063* (2013.01); *H05G 2/00* (2013.01); *H05H 1/22* (2013.01); *H05H 2277/10* (2013.01); *H05H 2277/11* (2013.01); *H05H 2277/113* (2013.01)

(58) Field of Classification Search
CPC  H05G 2/008; H05H 1/00; H05H 1/24; H05H 1/46; H05H 1/48; H05H 1/54; H05H 2277/00; H05H 2277/10; H05H 2277/11; H05H 2277/113; H05H 2277/116; H01J 15/00; H01J 15/02; H01J 15/04; H01J 27/00; H01J 27/02; H01J 27/022; H01J 35/00; H01J 35/02; H01J 35/025; H01J 35/04; H01J 35/06; H01J 35/08; H01J 35/14; H01J 49/00; H01J 49/10; H01J 49/105; H01J 61/62; H01J 63/08; H01J 65/04; H01J 65/042; H01J 2217/00; H01J 2217/04; H01J 2217/06; H01J 2217/10; H01J 2237/00; H01J 2237/006; H01J 2237/047; H01J 2237/0473; H01J 2237/04732; H01J 2237/06; H01J 2237/063; H01J 2237/08; H01J 2237/0802; H01J 2237/15; H01J 2237/152; H01J 2237/244; H01J 2237/2441; H01J 2237/24415; H01J 2237/32; H01J 2237/327; H01J 2893/00; H01J 2893/006; H01J 2893/0063; H01J 37/00; H01J 37/32; H01J 37/32009; H01J 37/32331; H01J 37/32339; H01J 37/32422; H01J 37/32431; H01J 37/3244; H01J 37/32449; H01J 37/32532; H01J 37/32568; H01J 37/3266; H01J 37/32669; H01J 37/32798; H01J 37/32908
See application file for complete search history.

(56) References Cited

U.S. PATENT DOCUMENTS

| | | | | |
|---|---|---|---|---|
| 7,782,914 B2 * | 8/2010 | Faure | .................. | H05H 15/00 372/25 |
| 2008/0067456 A1 * | 3/2008 | Kloepfel | ................ | H05G 2/003 250/504 R |
| 2008/0237498 A1 * | 10/2008 | MacFarlane | ........... | H05G 2/003 250/493.1 |
| 2008/0290304 A1 | 11/2008 | Neuhaus | | |
| 2011/0284778 A1 | 11/2011 | Neuhaus | | |
| 2012/0145930 A1 * | 6/2012 | Kuwabara | .............. | H05G 2/008 250/504 R |
| 2013/0077069 A1 * | 3/2013 | Mestrom | ................ | H05G 2/005 355/67 |

OTHER PUBLICATIONS

Ditmire, T., et al., "The Interaction of Intense Laser Pulses with Atomic Clusters", 1996, Phys. Rev. A, vol. 53, No. 5, pp. 3379-3402.*
Fuchs, Matthias, et al., "Laser-driven Soft X-ray Undulator Source", Nov. 2009, Nature Physics, vol. 5, pp. 826-829.*
European Patent Office, International Search Report in International Patent Application No. PCT/FR2012/051297 (Sep. 19, 2012).
State Intellectual Property Office of P.R.C., Office Action in Chinese Patent Application No. 201280038867.5 (Aug. 27, 2015).
Smith et al., "Characterization of a cryogenically cooled high-pressure gas jet for laser/cluster interaction experiments." *Review of Scientific Instruments*, vol. 39, No. 11, (Nov. 1998), pp. 3798-3804.
Fuchs, et al., "Laser-driven soft-X-ray undulator source", *Nature Physics 5*, (Sep. 2009), pp. 826-829, Supplementary Information to the manuscript.

* cited by examiner

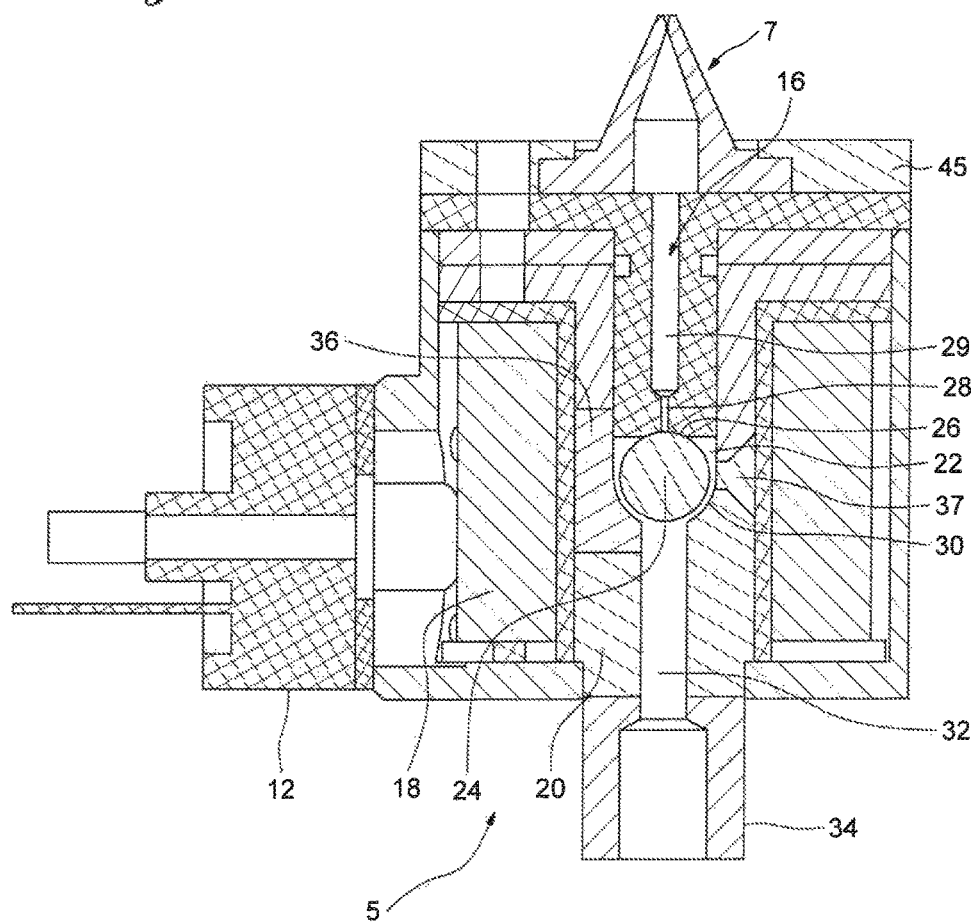

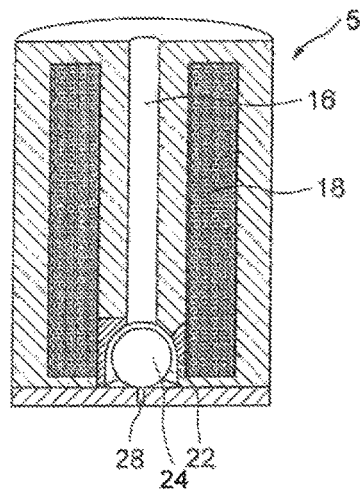
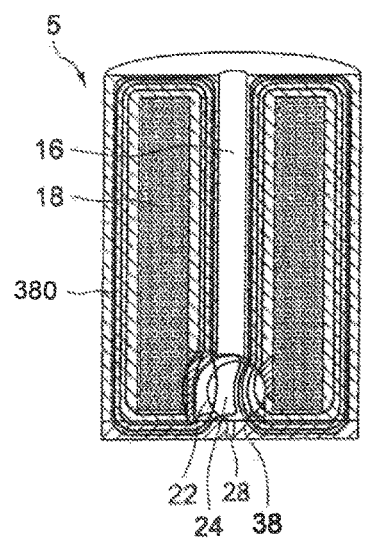
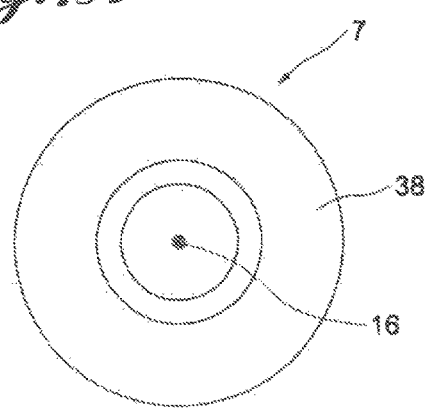
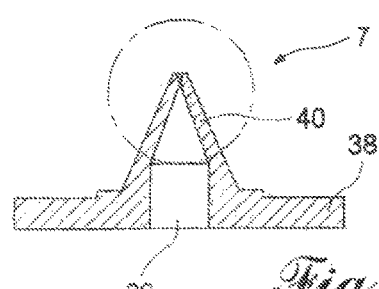
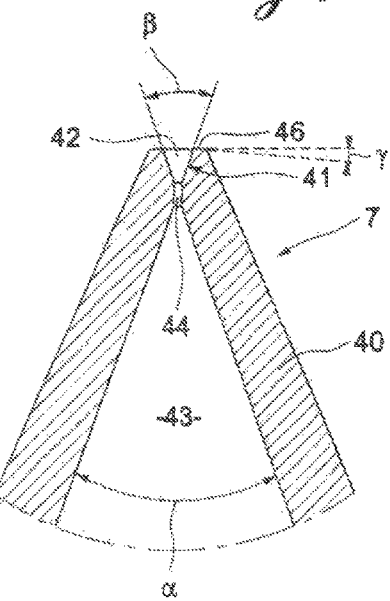

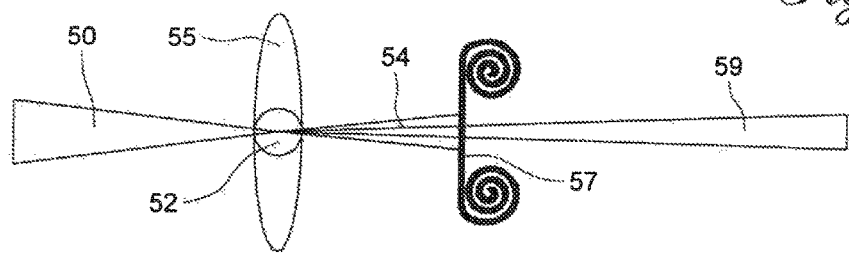
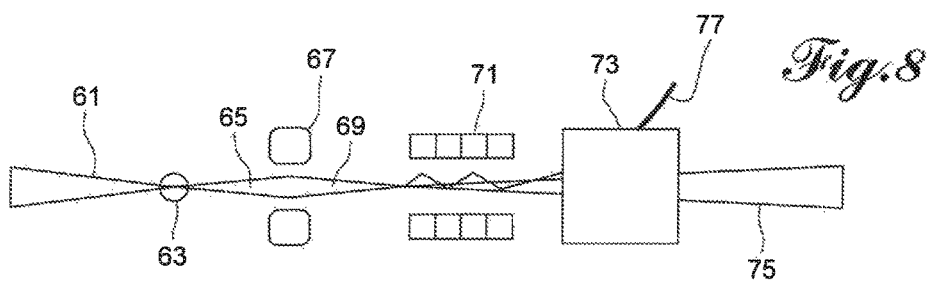
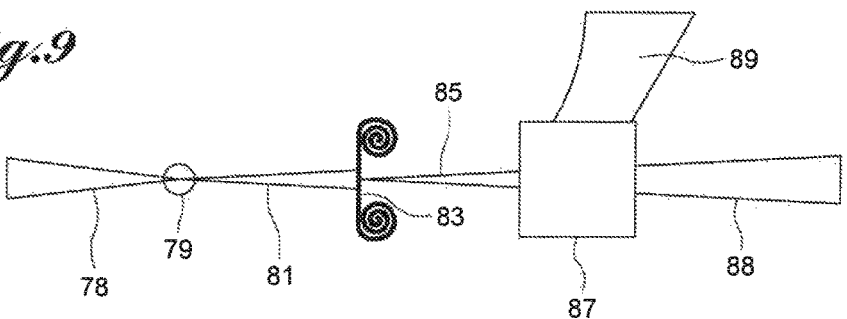
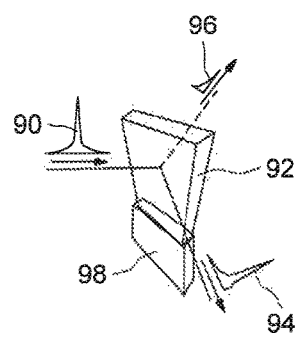

METHOD AND ARRANGEMENT FOR GENERATING A JET OF FLUID, METHOD AND SYSTEM FOR TRANSFORMING THE JET INTO A PLASMA, AND USES OF SAID SYSTEM

FIELD OF THE INVENTION

The invention relates to a method and an arrangement for generating a jet of fluid with strong atomic density as well as to a method and system for transforming such a jet of fluid into a plasma by means of a laser beam, as well as to methods for applying the transformation system.

BACKGROUND

Methods and systems of this type are already known, but do not give the possibility of obtaining jets of fluid with a sufficient rate and atomic density in order to ensure efficient utilization of the potential technical possibilities of these jets and notably of those which may result from interactions of these fluid jets with laser beams.

SUMMARY OF THE INVENTION

The object of the invention is to find a remedy to this drawback.

In order to achieve this object, the method for generating the jet of high density fluid is characterized in that it comprises the operation of generating by means of a high pressure fast solenoid valve, followed by a nozzle pipe mounted on the outlet opening of the solenoid valve, a pulsed fluid jet with submillimetric dimensions and with an atomic density of more than $10^{20}$ atoms-cm$^{-3}$.

According to a feature of the invention, the method is characterized in that the atomic density of the fluid jet has a value of $10^{21}$ atoms-cm$^{-3}$ or more.

According to another feature of the invention, the method is characterized in that fluid is a gas such as helium.

Still further according to another feature of the invention, the method is characterized in that the fluid is biphasic such as an aggregate jet.

According to further another feature of the invention, the method is characterized in that the fluid is a liquid such as water.

According to still another feature of the invention, an arrangement generating a jet of fluid of strong atomic density, for applying the method described above is characterized in that it comprises a source of pressurized fluid, a high pressure solenoid valve for fast opening and closing of the channel for the passage of the fluid through the solenoid valve, and a nozzle pipe adapted for accelerating and structuring the pulsed jet of fluid, produced by the solenoid valve.

According to yet another feature of the invention, the arrangement is characterized in that the solenoid valve includes a solenoid and a mobile element for fast opening and closing of the channel for the passage of the fluid through the solenoid valve, which is displaceable laterally to this channel, in its position for opening the channel, under the effect of the magnetic field produced by the solenoid and the return of which into its position for closing the channel occurs under the effect of the pressurized fluid.

According to still another feature of the invention, the arrangement is characterized in that the gap around the channel includes at the mobile element an asymmetry having the consequence of generating a magnetic field component oriented perpendicularly to the channel and intended to cause displacement of the mobile element towards its position for opening the channel.

The invention also relates to a method for generating a plasma, which is characterized in that a jet of fluid is used and in that a laser, the beam of which is oriented perpendicularly to the jets, is caused to act on the jet leaving the nozzle pipe, inside a vacuum chamber.

According to a feature of the invention, the method for generating a plasma is characterized in that a pulsed jet of fluid with strong atomic density but with a sufficiently small width is generated so that a very high speed pump such as a pump of the turbo-molecular type may be used for generating a vacuum in the chamber.

According to another feature of the invention, the method for generating a plasma is characterized in that a vacuum of the order of $10^{-7}$ bars is generated inside the chamber.

The invention also relates to a plasma generating system for applying the method for generating a plasma, which is characterized in that it comprises a source of a pressurized fluid, an arrangement generating a jet of fluid, a laser, the beam of which acts on the jet of fluid at the outlet of the nozzle pipe, a vacuum chamber in which is positioned the arrangement generating the jet and in which occurs the impact of the laser on the jet of fluid and in that it includes a pump for generating vacuum inside the chamber, which is of the very high speed type such as a turbo-molecular pump.

The invention also relates to a method for applying a system generating a plasma, which is characterized in that the system is used for producing ion beams with a narrow spectrum at a high rate in the direction of the laser and emission of ions with a wide spectrum at high rate in the direction perpendicular to the laser.

According to a feature of the invention, this method for applying the system is characterized in that an intense laser beam is used, consisting of one or several short pulses of the order of a few picoseconds and with an interval between the pulses of a few picoseconds, this laser beam is focused on a jet of fluid at a high rate and with an overcritical density for this laser.

According to another feature of the invention, the method for applying the system is characterized in that the beam of ions at a high rate exiting the plasma in the laser axis is filtered by advantageously using a mobile filter such as a sheet of aluminum from a few tens to a hundred micrometers in order to allow refreshing of the surface which the beam damages at each impact.

The invention further relates to a method for applying the system which is characterized in that the system is used for producing a beam at a high rate.

According to still another feature of the invention, the method for applying the system is characterized in that an intense laser pulse is focused in a jet of fluid at a high rate and strong density such as a density of the order of $10^{19}$ atoms/cm$^3$ for producing a slightly divergent electron beam and with short duration, this beam is spatially refocused and the refocused beam is passed through an undulator.

According to still another feature of the invention, the method for applying the system is characterized in that the beam having crossed the undulator is passed through a device which deviates the electrons and gives the possibility of obtaining a beam of X-rays exclusively.

According to still another feature of the invention, the method for applying the system is characterized in that an undulator consisting of a succession of magnets with alternating polarity is used so that the electrons undulate upon passing through the undulator and radiate X-rays forwards in the direction of the beam.

According to another feature of the invention, the method for applying the system is characterized in that the spectral range of the X-rays is varied by varying the period of the alternating magnets and their power.

The invention further relates to a method for applying the system, which is characterized in that this system is used for producing gamma beams at a high rate.

According to another feature of the invention, this method for applying the system is characterized in that the gamma beams at a high rate are produced by converting an electron beam at a high rate, obtained from the plasma produced by interaction of an intense laser pulse with a jet of gas at a high rate and of strong density such as a density of the order $10^{19}$ atoms/cm$^3$.

According to still another feature of the invention, the method for applying the system is characterized in that the intense laser pulse is focused in the jet of gas and uses focusing optics with a focal length adapted to the length of the jet so that the laser beam propagates regularly therein, without any filamentation.

According to still another feature of the invention, the method for applying the system is characterized in that electron beam is impacted by a mobile converter in order to cause emission of gamma rays due to the slowing down of electrons by collision on the atoms of the converter.

According to further another feature of the invention, the method for applying the system is characterized in that a device such as a bipolar magnet is used for deviating the electrons and for obtaining a beam of gamma rays at a higher rate.

The invention further relates to a method for applying the system, which is characterized in that the system is used for achieving cleaning in time of intense pulses of the laser by means of the jet of fluid.

According to a feature of the invention, the method is characterized in that the laser pulse to be cleaned is made incident on a jet of fluid with an overcritical density for the wavelength of the laser so that the parasitic light of the pulse does not produce breakdown of the plasma and is translucent to this light and that the breakdown only occurs through the useful portion of the laser pulse which is then reflected by the jet of fluid.

The invention further relates to a method for applying the system, which is characterized in that this system is used for achieving space and time compression of the laser pulses.

According to a feature of the invention, the method is characterized in that an intense laser pulse to be compressed is focused in the jet of gas of high rate and with strong density, such as a density of the order of $10^{19}$ atoms/cm$^3$ and ensures that short wavelengths of the spectrum of the pulse will arrive on the plasma before the large wavelengths so that the slower propagation of the short wavelengths in the plasma causes recompression of the pulse in time.

BRIEF DESCRIPTION OF DRAWING FIGURES

The invention will be better understood and other objects, details advantages thereof will become more clearly apparent during the description which follows, made with reference to the appended drawings, illustrating an embodiment of the invention, and wherein:

FIGS. 2A and 2B are respectively perspective and axial sectional views of a solenoid valve and nozzle pipe assembly of the arrangement according to FIG. 1;

FIGS. 3A and 3B are two schematic axial sectional views of another version of a solenoid valve which may be used in an installation according to FIG. 1, in order to explain the operating principle of such a solenoid valve;

FIGS. 4A, 4B and 4C are three views of a nozzle pipe according to an invention, FIG. 4A being a top view, FIG. 4B an axial sectional view along the line IV-IV of FIG. 4A and FIG. 4C is a view at a larger scale of the details surrounded by a circle in FIG. 4B;

FIG. 7 is a schematic view illustrating a first application of the invention intended for producing ion beams with a narrow spectrum at a higher rate in the direction of the laser and emissions of ions with a wide spectrum and a higher rate in the direction perpendicular to the laser;

FIG. 8 is a schematic view illustrating a second application of the invention allowing the production of X beams at a higher rate;

FIG. 9 is a schematic view illustrating a further application of the invention, allowing the production of gamma beams at a higher rate;

FIG. 10 is a schematic view further illustrating another application of the invention allowing cleaning in time of an intense laser pulse.

DETAILED DESCRIPTION

Figure 1:
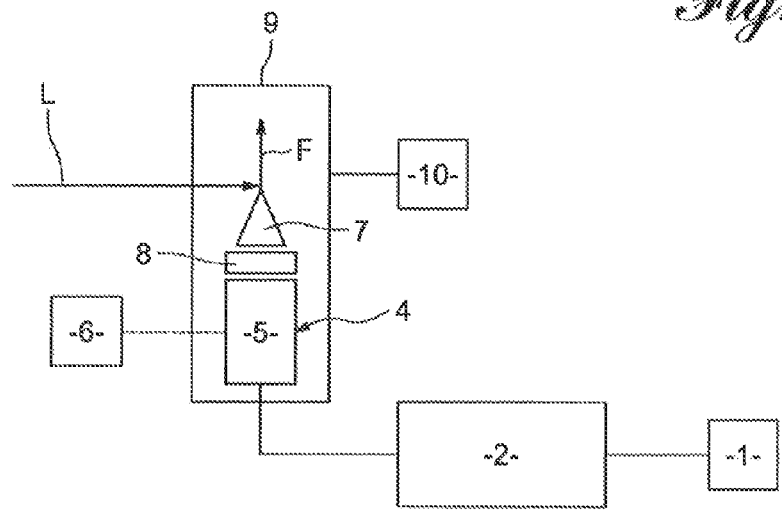
FIG. 1 is a schematic view of an arrangement according to the invention.

FIG. 1 illustrates, as example, an arrangement generating a plasma by interaction of a millimetric or submillimetric jet of fluid at a high rate and strong density which may be greater than $10^{19}$ atoms/cm$^3$ and may range up to $10^{21}$ atoms/cm$^3$ and more. The system essentially includes a source 1 of a fluid such as a gas, for example helium, or a liquid such as water, which is transmitted to a supercharger 2 which in turn transmits the strongly compressed fluid to a device 4 for generating the pulsed jet of fluid indicated by the arrow F and formed by a succession of pulses with a duration from a few microseconds and with the aforementioned density, of more than $10^{19}$ atoms/cm$^3$.

The generating device 4 includes a solenoid valve 5, the mobile element of which has very low inertia and which therefore has a very short response time. As an example, the opening and the closing of the solenoid valve maybe accomplished in less than 3 milliseconds, i.e. at a rate of about 300 Hz. This solenoid valve which will be described in more detail later on is controlled by an electric control device 6. A nozzle pipe 7 is mounted on the outlet of the solenoid valve via an adaptor 8 which is for example screwed onto the outlet of the solenoid valve. The generating device 4 is confined in a sealed chamber 9 in which a vacuum is generated for example of $10^{-7}$ bars by means of a very high speed pump, for example of the turbo-molecular type 10. A substantial vacuum preferably of this order or less is desirable if not necessary for avoiding interactions between the laser and the air molecules remaining inside the chamber.

The generating device 4, by means of the nozzle pipe 7, is adapted so as to be able to accelerate and structure the flow of fluid, when the solenoid valve is actuated, so that this flow has at the outlet of the nozzle pipe the properties desired by the operator.

If the jet of fluid exiting the pipe 7 has to be transformed into a plasma, a laser beam symbolized by the arrow L is caused to act on the jet of fluid materialized by the arrow F, which exits the nozzle pipe.

Figure 2A:
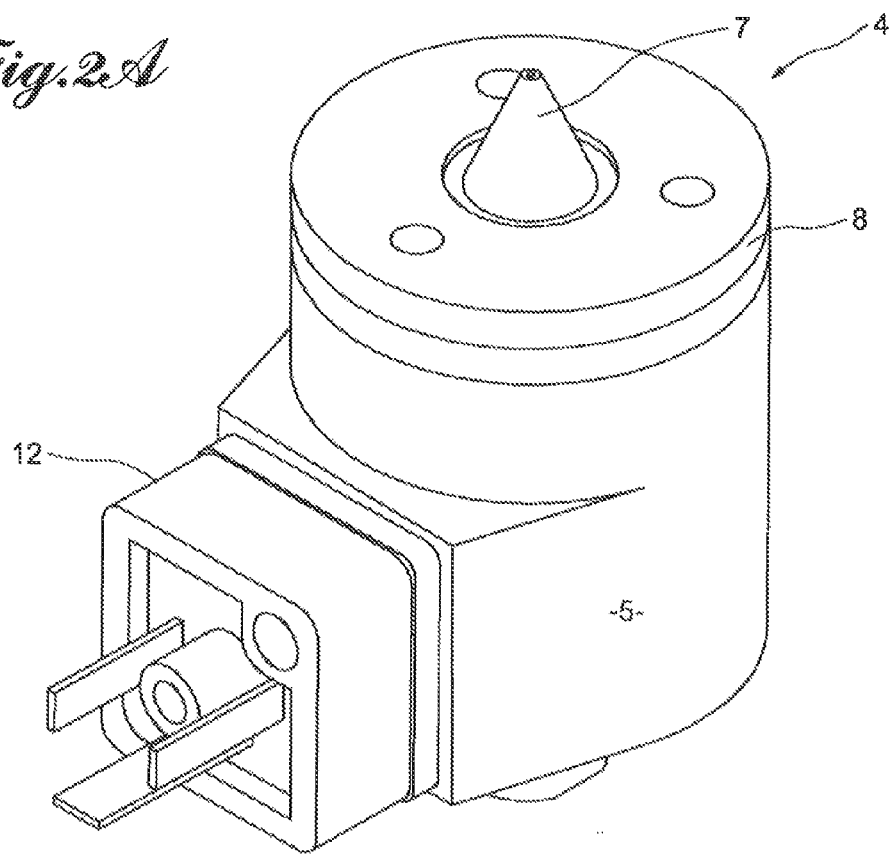

FIGS. 2A and 2B illustrate as an example, a device for generating a jet of fluid at a high rate and with a strong density, as indicated in 4 in FIG. 1. FIGS. 2A and 2B illustrate in 4 the solenoid valve, in 8 the adaptor and in 7 the nozzle pipe. The reference 12 indicates the connector to the device for controlling the solenoid valve.

The electro-valve 5 includes a cylindrical body which is axially crossed, in its center, by a channel 16 and houses a solenoid 18 which is co-axially positioned around the channel while leaving between this channel and the solenoid a wall 20 in a magnetizable material and through which therefore pass the lines of the magnetic field generated by the solenoid when it is energized, i.e. when an electric current flows through it. The connector 12 is made in the form of an endpiece radial to the cylindrical body.

As shown in FIG. 2B, the wall 20 delimits in the body 14, a valve chamber 22 which houses, in the illustrated example, a ball 24 in a thermomagnetic material and which forms the mobile element for opening and closing the axial channel of the valve. The chamber is sufficiently wide so as to allow lateral movement of the mobile element 24, perpendicularly to the axis of the channel.

The chamber is therefore laterally delimited by the wall 20 and at the top in the figure, perpendicularly to the wall 20 by a substantially planar wall 26 at the center of which opens the channel 16 into the chamber 22. This portion of the channel noted as 28 is narrower than the upper channel portion 29 which communicates with the nozzle pipe 7. In the rest condition, when the solenoid valve is not energized, the mobile element 24 obturates the channel 28, the opening area of which in the chamber 22 is, for this purpose, configured so as to form the seat for sealing this element 24.

On the side axially opposed to the transverse wall 26, the chamber 22 has a concave face 30 with a shape of a spherical cap, mating the element 24, and at the center of which opens the channel 16, here formed by a wider channel portion 32 which is intended to communicate with the overpresser 2. For this purpose, the solenoid valve includes an axial connection endpiece 34.

The element in the shape of a ball 24 is laterally displaceable between its central position on the seat 26 in which the element closes the channel 16 by obturating the channel portion 28 and a laterally shifted position of the seat in which the channel is open and allows flow of the pressurized fluid from the overpresser 2 to the nozzle pipe 7.

This lateral displacement for opening the channel 16 is obtained by energizing the solenoid 18 under the effect of the magnetic field produced by the latter. For this purpose, the magnetic field should have at the mobile element 24, a component which is oriented perpendicularly to the channel. This component is obtained by creating an irregularity in the gap portion of the wall 20 at the ball 24. For this purpose, this wall therefore includes at the ball, inserts 36 and 37, which are positioned on the drawing at the left and at the right of the ball 24, respectively. These inserts have different magnetic sensitivity from the remainder of the wall 20. By giving these inserts various shapes, as illustrated in the figure, an asymmetry is generated in the magnetic circuit which generates the perpendicular component of the magnetic field, which causes the lateral displacement of the ball. With the purpose of energizing the solenoid, the ball returns into its central position in the chamber.

FIGS. 3A, 3B, although schematically showing another version of a solenoid valve, however of the same type of structure and operation, illustrates what has just been said. Indeed, FIG. 3A shows the ball 24 for closing the channel 16 in its position for obturating the channel and FIG. 3B shows this ball in its laterally shifted position for opening the channel, under the effect of the magnetic field produced by the solenoid 18. FIG. 3B illustrates in 380 the lines of the magnetic field which has at the ball, lateral protrusions due to the asymmetry of the gap created by the inserts 36, 37. Therefore, the magnetic field at the ball 24 has a component perpendicular to the channel 16 which therefore generates the lateral displacement force of this ball.

Thus, when the solenoid is energized, the body 24 switches from its rest position to a side of the seat 26, because of the asymmetry of the magnetic field, which allows the fluid to freely circulate through the channel 16. Upon stopping the energization, the body 24 switches back to its rest position because of the friction of the circulating fluid, which ensures closing of the channel 16.

The switching system ensures a fast response. As an example, the opening and the closing of the solenoid valve may be accomplished in less than 3 milliseconds, therefore at a rate of about 300 Hz, and the magnetic force developed by the solenoid allows the movement of the mobile body, i.e. of the ball 24 pressed against its seat by a fluid for example of the order of 400 bars at room temperature, which may increase up to 1,000 bars. The controllable electric power supply gives a possibility of delivering the required electric power for a duration which may be adjusted by the operator, as an example from one picosecond. This gives the possibility of finely varying the oscillation period of the ball 24 and therefore the amount of fluid which passes into the solenoid valve, i.e. the flow rate, and finally the density, which the solenoid valve may deliver at the outlet into the nozzle pipe 7. Also, for a set period of oscillation, it is possible to vary the pressure of the fluid at the inlet of the solenoid valve and therefore vary the flow rate at the outlet.

FIGS. 4A to 4C show the outlet pipe 7 which is positioned on the outlet of the solenoid valve, via the adaptor 8 attached on the solenoid valve. The latter is screwed onto the outlet of the valve.

The nozzle pipe 7 is attached on the adaptor 8 and secured to the latter by a cap 45 which is attached on the solenoid valve with screws, the passage holes of which are indicated in 45. It should be noted that a circular rubber gasket 45 surrounded by a metal ring is provided for ensuring the seal of the high pressure circuit. The metal ring ensures homogeneous squeezing of the gasket against the adaptor and avoids displacement of the gasket when high pressure is applied.

In the illustrated example, the nozzle pipe includes a base 38 with a shape of a disk, the central portion of which is pierced through a central orifice 39 for letting through the fluid under pressure, which is in alignment with the channel 16 crossing the solenoid valve, and a conical tubular portion 40 which shrinks in the direction of the outlet orifice 41, the tip portion of which communicates with the inside of the conical internal space 43 of the nozzle pipe through a short cylindrical portion 44. Thus, the pipe is of the conversion/diversion type producing supersonic flow. Of course, pipes of another type may be contemplated, for example a nozzle pipe with a cylindrical outlet orifice which may produce a sonic or subsonic fluid flow.

As regards the pipe of FIG. 4, concerning its dimension, as an example, the convergent $\alpha$ and divergent $\beta$ angles may both be of the order of 40° and the diameter of the small cylindrical portion 44 between the convergent and divergent portions may have a diameter of 0.1 mm. The divergent conical portion 42 may have at its outlet a diameter of 0.4 mm.

Figure 5:
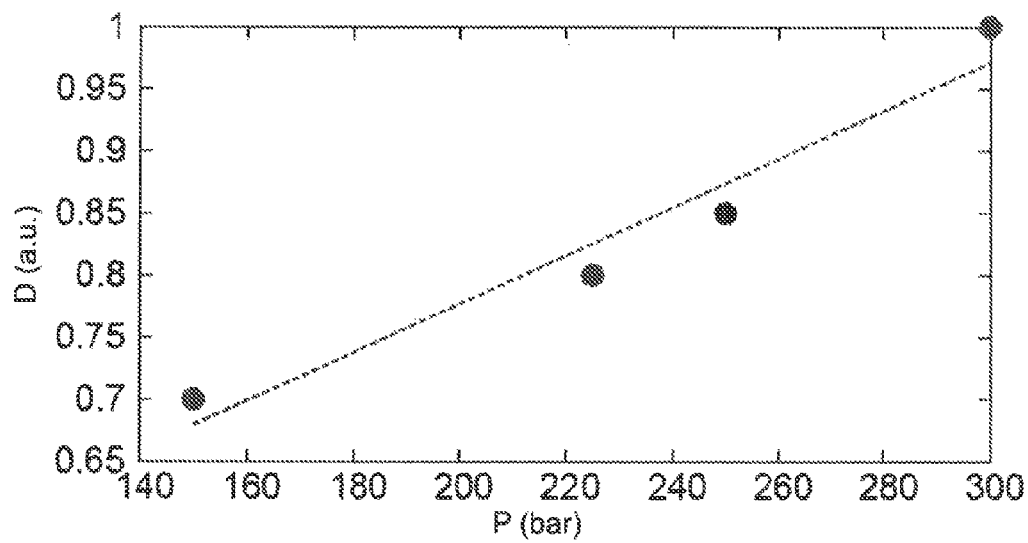
FIG. 5 illustrates as a curve the density D of the jet of fluid versus the pressure P produced by the super charger.
Figure 6:
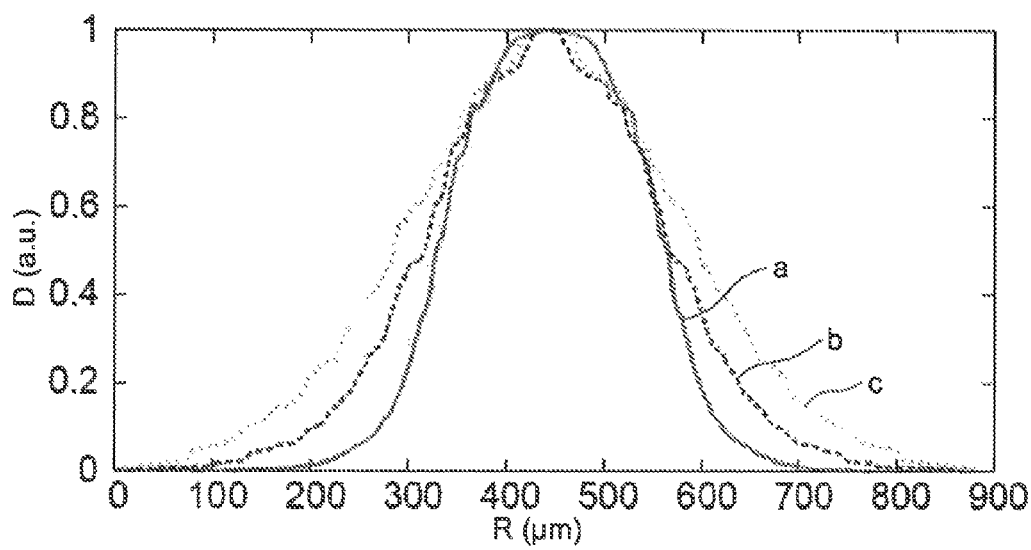
FIG. 6 shows, as a curve, the density of the fluid versus the radius R.

The use of the arrangement generating a jet of fluid, equipped with an outlet pipe further has the considerable advantage that the width of the jet and the density of the latter are independent. FIGS. 5 and 6 allow an explanation of this independence.

FIG. 5 shows density D versus pressure P. The latter is indicated in bars while the density is normalized. The points are values which were measured. The time-dependent change of the density versus pressure may be illustrated as a straight line indicating that the density gradually increases with the pressure.

FIG. 6 illustrates for several heights, i.e. distances from the outlet of the pipe, the reduction of the density of a jet from its longitudinal axis, perpendicularly to the latter. The curves a, b and c are made for heights of 100 micrometers, 200 micrometers and 300 micrometers, respectively. The ordinate indicates a density D in the form of normalized values, i.e. every time based on the maximum density. The abscissa defines the locations R in the direction perpendicular to the jet, in micrometers. FIG. 5 shows that it is possible to continuously vary the peak density by varying the pressure and it emerges from FIG. 6 that it is possible to select a given width, i.e. a radius, by selecting the height at which the laser acts on the beam.

Therefore, if the height is set and thus the width, it is then possible to freely vary the density, independently.

The whole of the arrangement for generating a high density fluid according to the invention operates under a secondary vacuum since it is confined in the sealed chamber 9. The arrangement works at high rates depending on the delivered throughput. The rates may be high when the throughput is relatively small and the flow rate is high in the case of low rates, this because of the volume of the pumped chamber and of the yield of the vacuum pumps, which are advantageously of the turbo-molecular type.

As it was indicated above, the nozzle pipe structures the flow. The size of the latter determines the size of the plasma. The pressure which feeds the nozzle pipe determines the density. For a given pipe, it is therefore possible to vary the density independently by varying the pressure and the length.

It should be noted that the impact of the laser beam is made at a very small distance from the outlet of the nozzle pipe in the area of the stronger density of the fluid pulses, of the order of 100 to 200 micrometers for example. The laser beam will be focused on the pulses. Given that the beam thus has some conicity, with the diameter shrinking in the direction of the impact on the pulse, the front face 46 instead of being perpendicular to the axis of the outlet, may be slightly tilted rearwards from the outlet by an angle γ, so that the laser beam may act on the pulse as close as possible to the nozzle pipe outlet.

As regards the fluid used, gas such as helium is advantageously used but the use of any other gas may be contemplated. It would also be possible to use a liquid which would then be adapted for efficient coupling between the plasma and the laser.

The thereby obtained system gives a possibility of making a jet of fluid formed by a sequence of pulses at a high rate and with a strong density which may be greater than $10^{19}$ as far as the critical atomic density of $10^{21}$ atoms·cm$^{-3}$ for a Ti:SAPPHIRE laser. The rate may be greater than a few hertz, up to 300 hertz and even more. The gas may be provided by the overpresser at a pressure of 400 bars at room temperature. This pressure may be greater and, if necessary range up to 1,000 bars. As this was specified above, the pressure which prevails inside the chamber is of $10^{-7}$ bars. Because of the short duration of the pulses generated by the valve and in spite of the strong densities and of the low mass of the fluid pulses due to the small dimensions of the pipe, it is possible to obtain this vacuum inside the chamber, by means of vacuum pumps, for example of the turbo-molecular type without these pumps deteriorating. By means of high rate and high density jets which may be produced by the arrangement according to the invention, the invention makes it possible to explore domains of density and of fluid jet rate which could not be explored up to now. The invention thus opens multiple applications, certain of which will be described hereafter as examples.

These applications are divided into two main fields of application, i.e. the generation of particles and of radiation, on the one hand, and the shaping of intense laser beams on the other hand.

With reference to the schematic FIG. 7, a method and a system for producing beams of ions with a narrow spectrum at a high rate in the direction of the laser and emitting ions with a wide spectrum at a high rate in the direction perpendicular to the laser are first of all described. A spectrum is considered as being narrow when the variation of the energy ΔE relatively to the average energy E of the spectrum is less than 1%.

For this purpose, an intense laser beam is used for example of $10^{17}$ W/cm$^2$ to $10^{22}$ W/cm$^2$, consisting of one or several short pulses with a duration per pulse of less than a few picoseconds and with a duration between the pulses of a few picoseconds. This pulse may be structured in different ways in a way known per se, by means of a final amplifier for $CO_2$ lasers which already include structured pulses or more generally in an optical way by sub-dividing a main pulse and then by delaying by a desired delay each sub-pulse obtained after division. The intense structured pulse generates a plasma from the fluid upon the impact with the latter, i.e. it generates a free electric charge, formed by ions and electrons, by "breakdown" of the plasma as soon as the fluence of the laser exceeds about 1 J/cm$^2$ Of course, it would also be possible to use a single pulse instead of a structured pulse formed with several sub-pulses. The benefit of using a structured pulse rather than a single pulse is to facilitate the sinking of the target by a laser of identical average power, but with a lower peak power. Indeed, each pulse acts like a piston by the radiative pressure which it exerts on the plasma which is thus drilled erratically, this force being proportional to the intensity divided by the speed of light. Like with a hammer and a nail, it is easier to pierce the material with this sequential device. This is not indispensable but simply more economical in terms of average power per laser pulse.

This effective piercing allows the laser to transfer its energy over the whole volume to the electrons of the plasma which heat up and, by plasma physics, give the possibility of generating a beam of ions having a narrow spectrum wherein all the ions have quasi the same energy to within a few percent, oriented in the direction of propagation of the laser. An emission of ions also mainly exists in the direction perpendicular to the propagation of the laser, but this is not in the form of a directive beam and the emitted spectrum is wide.

Therefore, a device according to FIG. 7 may therefore be contemplated, comprising a laser with a pulse either structured or not, focused on a jet of fluid at a high rate and of overcritical density for this laser. In the case of a $CO_2$ laser, the density is $10^{19}$ cm$^{-3}$, for a Ti:SAPPHIRE laser the density would be $10^{21}$ cm$^{-3}$. In FIG. 7 the focused structured laser beam is indicated in 50. The impact of the laser on the jet of fluid at a high rate indicated in 52 generates a beam of ions 54 with a narrow spectrum at a high rate in the axis of the laser and causes an emission of a wide spectrum 55 in the perpendicular direction.

In order to filter the laser, a circulating filter 57 is used, for example an aluminum sheet with a thickness of a few tens to a hundred micrometers which runs at a speed of 1 cm/s or more, which gives the possibility of refreshing the surface which the laser damages at each impact. FIG. 7 shows the beam of ions at a high rate, with a narrow spectrum, thereby obtained in 59.

This beam may be used for depositing the dose, i.e. energy into the material at a given thickness because the spectrum is narrow. The wide emission 55 may be used for probing regions with a strong electric field like our plasma. A map coded in a field gradient contrast is obtained.

FIG. 8 illustrates another application of the invention, i.e. the production of X beams with a high rate by injecting a beam of electrons at a high rate refocused in an undulator.

An intense laser pulse noted as 61 is focused in a jet 63 of gas at a high rate and with a density of about $10^{-19}$ atoms/cm$^3$. Focusing optics are used with a focal length adapted to the length of the jet so that the laser propagates them regularly without filamentation, i.e. without exploding like lightning which is branched. Experiments in the laboratories have shown that certain electrons, on the path of the laser, may be "trapped" by the laser field, i.e. they follow the laser, and are accelerated to high energies all along the propagation. The final energy of the electrons depends on the area of the jet where the electrons are injected so as to be trapped in the wake of the laser. The energy of the electrons will be high when the injection area is localized at the entry of the jet and relatively lower in the case of localization at the outlet. The electrons emerge from the plasma in the form of a slightly divergent beam 65 and run in time, with a duration depending on that of the laser pulse. The high rate beam 65 is spatially refocused by means of a quadrupolar magnet 67 or several quadrupolar magnets mounted in series. By using several quadrupoles it is possible to sequentially perform corrections of the path of the electrons to be refocused, which is technically simpler to carry out and generates less errors than with a single more powerful quadrupolar magnet. The value of the magnetic fields of the magnets is related to the dispersion to the energy of the electrons of the incident beam. The refocused and therefore convergent electron beam, noted as 69, is injected into an undulator 71. The latter consists of a succession of magnets with alternating polarities so that the electrons "undulate" upon passing and radiate X-rays forwards according to the physical principle of radiative emission by an accelerated electron. The period of the alternating magnets and their power define the spectral range of the X emission. If the magnets are adjusted in agreement with the injection energy of the electrons, the power of the X emission increases as the electrons advance while undulating in the undulator and the obtained x spectrum is narrow, i.e. there is agreement between the phase and the constructive emission. A bipolar magnet 73 is placed at the outlet of the undulator in order to deviate the electrons and only retain the beam of X-rays. The latter is indicated by reference 75 while the deviated electron beam is indicated in 77. The beam 75 is a beam of X particles at a high rate and forms a pulsed X laser.

The device according to FIG. 8 gives the possibility of adjusting the density of the jet of gas, the energy of the electrons in order to have optimum agreement with the characteristics of the quadrupolar magnets and of the undulator.

Therefore, FIG. 8 illustrates the implementation of a pulse x laser from the interaction of an intense laser 61 and of a high rate jet 63.

FIG. 9 shows a third application of the invention, i.e. a system for producing high rate gamma beams by conversion of a high rate electron beam by a circulating converter.

In this application, an intense laser pulse 78 is focused in a jet of gas 79 at a high rate and with a density of about $10^{19}$ atoms/cm$^3$. In order to focus the laser, focalization optics are used with a focal length adapted to the length of the jet so that the laser propagates therein regularly, without any filamentation, i.e. without exploding like lightning which is branched. As this has just been explained within the scope of the second application, laboratory experiments have shown that certain electrons on the path of the laser may be "trapped" by the field of the laser and be accelerated at high energies all along the propagation. As indicated above, the final energy of the electrons depends on the area of the jet where the electrons are injected so as to be trapped in the wake of the laser. The electrons emerge from the plasma in the form of a slightly divergent beam 81 and run over time, with a duration depending on that of the laser pulse. The electron beam includes a circulating converter 83, for example typically a tantalum sheet with a thickness of 1 mm, which moves at a speed of 1 cm/s or more, which allows refreshing of the surface which the laser damages at each impact. While penetrating into the converter, the electrons are slowed down by collision of atoms, which causes emission of gamma rays in the form of beams towards the front, by an effect known as "Bremsstrahlung". A beam of gamma rays with a high rate noted as 85 is thereby obtained. This beam of electrons having crossed the converter between a bipolar magnet 87 which gives the possibility of obtaining a beam of gamma rays as a high rate 88 and causes deviation of the electrons in the form of a deviated electron beam 89.

The device according to FIG. 9 therefore gives the possibility of obtaining a beam of gamma rays at a high rate. For a given position of the circulating converter 83 relatively to the jet 79, by varying the thickness of the converter it is possible to vary the number of gamma rays obtained at the output, i.e. the luminosity of the gamma source, and the size of the source. These gamma rays give the possibility of probing dense material and obtaining by absorption contrast, radio graphic maps which may be used for obtaining the tomography of an object with a typical resolution of 50 μm.

A fourth application will be described hereafter, relating to the second field of the shaping of intense laser pulses. This application recommends time cleaning of intense pulses by induction of a plasma mirror according to FIG. 10.

In an intense laser pulse, the main pulse is preceded with parasitic light (amplified spontaneous emission or ASE) which may be bothersome for interaction uses when its intensity is moderate since it may cause premature breakdown of the material with which the interaction is desirably achieved, which makes the structure of the target undetermined. This parasitic light is of the same wavelength as the main pulse and with the same polarization. Optical selection is therefore not easy.

On the other hand, it is possible to discriminate the parasitic light by its intensity which is much lower than that of the main pulse.

As shown in FIG. 10, the laser pulse to be filtered, indicated by reference 90, is incident on a jet of fluid 92 with an overcritical density for the wavelength of the laser used. The jet 92 is translucent to the pulse as long as breakdown of the plasma has not occurred. Thus, as long as the fluence of the laser (energy per surface area of the laser beam) does not reach 1 J/cm$^2$ or, which is equivalent for a given pulse datum, that the intensity does not reach $10^{10}$ w/cm$^2$ the jet of fluid remains transparent and the pulses pass through. As soon as these limits are exceeded, the fluid breaks down and an overcritical plasma develops at the surface, into which the laser can no longer penetrate. The remainder of the pulse is therefore reflected.

FIG. 10 shows in 94 the reflected laser pulse and in 96 the laser pulse which crosses the jet of fluid 92 exiting the nozzle pipe noted as 98.

In this application, the jet of fluid 92 at high density notably a liquid, and at the higher rate, therefore operates like a selective mirror which absorbs the parasitic moderate laser intensities at the beginning of the incident pulse 90 and reflects the strong intensities in the form of a pulse 94 which may be used for producing an interaction under more controlled conditions.

A fifth application relating to this field of the shaping of intense laser pulses ensures space and time compression of the pulses.

In this application, an intense laser pulse is focused in the jet of gas at a higher rate and with a density of about $10^{19}$ atoms/cm$^3$. Focusing optics are used with a focal length adapted to the length of the jet so that the laser propagates therein regularly, without any filamentation.

This pulse in fact consists of several wavelengths with relative phase shifts. Now, the plasma has the effect of inducing different phase delays according to the wavelength. Short wavelengths travel less faster in plasma than large wavelengths. Therefore, if the relative phase shift comprised between two different wavelengths of the laser pulse at the entry of the plasma is selected wisely, i.e. if the short wavelengths arrive on the plasma before the large wavelengths (it is said that the frequencies are derived positively) in a way that the travel in the plasma may resynchronize the components, i.e. put the spectral components back into phase, the plasma may contribute to the recompressing the pulse in time. The frequency drift may be obtained in a way known per se, for example by means of a device marketed under the name of DAZZLER.

Recompression in time by putting the components of the spectrum in phase directly comes from the Fourier relationship dt.DW=constant. Thus, a wide spectral content in phase DW of a pulse gives a short duration dt to the pulse. It is therefore possible to obtain at the output a shorter pulse in time and more intense if the plasma has not absorbed too much energy. It should be noted that this principle is widely explained in the literature. This type of compression is achieved up to now with gratings which are worn over time and only support rates of less than a few Hertz and have an energy efficiency of 60% (transmitted energy rate). The device according to the invention gives the possibility of obtaining a compression with a jet of fluid at a high rate with an energy efficiency of about 20%. Also, the plasma formed by the intense pulse may cause spatial focusing of the pulse by the Kerr effect and therefore intensify the pulse at the outlet of the jet.

It has just been demonstrated that the invention gives the possibility of attaining atomic densities of more than $10^{21}$ atoms/cm$^3$. By this feature, the invention gives the possibility of attaining what is called the critical plasma density from which a power laser which ionizes the gas of the jet leaving the pipe as a plasma, can no longer propagate. This physical density is given by the expression:

$$N_c\,[\text{cm}^{-3}] \sim 1.1 \times 10^{21}/L^2\,[\mu\text{m}]$$

wherein L is the wavelength of the laser used.

Therefore, with the invention it is possible to obtain the critical atomic density for any power laser with a wavelength above 0.750 micrometers. In particular, it is possible to attain the critical density for titanium: SAPPHIRE lasers (L=0.81 µm) which forms the large majority of power lasers presently used in science. This has a strong benefit since, from this density, the laser-plasma interaction ensures very efficient coupling, i.e. an almost total conversion of the laser energy into an internal energy of the plasma.

On the other hand, with the invention it is possible to obtain a non-linear time compression of intense laser pulses. For this purpose, an intense laser pulse is focused in the jet of gas at a higher rate with a density of about $10^{19}$ atoms/cm$^3$. Focusing optics are used adapted to the length of the jet so that the laser propagates therein regularly without any filamentation. When the intense pulse crosses the jet of gas, it directly modifies the optical index of the plasma, on the one hand and generates a plasma wave with very high amplitude which moves with the pulse, on the other hand. Both of these non-linear effects act in return on the pulse in the frequency domain, which has a consequence in the time domain of having the rear of the pulse travel faster than the front, and results in compression of the pulse. Through this process, the short and intense pulse may be compressed in time for example by a factor three over a few millimeters of gas, and therefore produce ultra intense pulses without any risk of destroying the structure which compresses. The use of a high rate and high density may make this process feasible at a high rate over only about 100 micrometers, which is an alternative to the techniques presently in use for shaping intense lasers at a high rate.

The invention claimed is:

1. A method for generating a pulsed jet of fluid comprising:
    generating, with a solenoid valve, under a pressure of at least 400 bars, and a nozzle pipe mounted on an outlet aperture of the solenoid valve, a pulsed jet of fluid with submillimetric dimensions and an atomic density of more than $10^{20}$ atoms-cm$^{-3}$, wherein the solenoid valve includes
    a solenoid,
    a mobile element for opening and closing a channel for the passage of the fluid through the solenoid valve, wherein the mobile element
        is displaceable perpendicularly to the channel, in opening the channel, in response a magnetic field produced by the solenoid, and
        closes the channel in response to pressure from the fluid, and
    a wall of a magnetizable material around the channel and having an asymmetry at the mobile element, and the method further includes energizing the solenoid, thereby producing an asymmetrical magnetic field having a component oriented perpendicular to the channel, displacing the mobile element, and opening the channel.

2. The method according to claim 1, wherein the atomic density of the pulsed jet of fluid is at least $10^{21}$ atoms-cm$^{-3}$.

3. The method according to claim 1, wherein the fluid is a gas.

4. The method according to claim 1, wherein the fluid is biphasic.

5. The method according to claim 1, wherein the fluid is a liquid.

6. An apparatus for generating a pulsed jet of fluid comprising:
a source of pressurized fluid,
a solenoid valve, under a pressure of at least 400 bars, opening and closing a channel for passage of the fluid through the solenoid valve to generate the pulsed jet of the fluid, and
a nozzle pipe accelerating and shaping the pulsed jet of the fluid that is produced by the solenoid valve to have submillimetric dimensions, wherein the solenoid valve includes
a solenoid,
a mobile element for opening and closing the channel for the passage of the fluid through the solenoid valve, wherein the mobile element
is displaceable perpendicularly to the channel, in opening the channel, in response a magnetic field produced by the solenoid, and
closes the channel in response to pressure from the fluid, and
a wall of a magnetizable material around the channel and having an asymmetry at the mobile element so that, when the solenoid is energized, an asymmetrical magnetic field having a component oriented perpendicular to the channel displaces the mobile element and opens the channel.

7. A method for generating a plasma comprising:
generating, with a solenoid valve under a pressure of at least 400 bars and a nozzle pipe mounted on an outlet aperture of the solenoid valve, a pulsed jet of a fluid; and
applying a laser beam perpendicular to the pulsed jet of the fluid leaving the nozzle pipe, in a vacuum chamber, wherein the solenoid valve includes
a solenoid,
a mobile element for opening and closing a channel for the passage of the fluid through the solenoid valve, wherein the mobile element
is displaceable perpendicularly to the channel, in opening the channel, in response a magnetic field produced by the solenoid, and
closes the channel in response to pressure from the fluid, and
a wall of a magnetizable material around the channel and having an asymmetry at the mobile element, and the method further includes energizing the solenoid, thereby producing an asymmetrical magnetic field having a component oriented perpendicular to the channel, displacing the mobile element, and opening the channel.

8. The method according to claim 7 wherein the pulsed jet of fluid has a sufficiently small width so that the vacuum may be generated by a vacuum pump.

9. The method according to claim 7 wherein the vacuum is of the order of $10^{-7}$ bars.

10. A system for generating a plasma comprising:
a source of pressurized fluid,
a solenoid valve, under a pressure of at least 400 bars, opening and closing a channel for passage of the fluid through the solenoid valve to produce a pulsed jet of the fluid,
a nozzle pipe accelerating and shaping the pulsed jet of the fluid to have submillimetric dimensions,
a laser producing a laser beam which acts on the pulsed jet of fluid at an outlet of the nozzle pipe,
a vacuum chamber containing the solenoid valve, the nozzle, and the laser and in which the laser beam acts on the pulsed jet of fluid, and
a pump for generating a vacuum inside the vacuum chamber, wherein the solenoid valve includes
a solenoid,
a mobile element for opening and closing the channel for the passage of the fluid through the solenoid valve, wherein the mobile element
is displaceable perpendicularly to the channel, in opening the channel, in response a magnetic field produced by the solenoid, and
closes the channel in response to pressure from the fluid, and
a wall of a magnetizable material around the channel and having an asymmetry at the mobile element so that, when the solenoid is energized, an asymmetrical magnetic field having a component oriented perpendicular to the channel displaces the mobile element and opens the channel.

11. The method according to claim 7, including producing beams of ions, wherein all ions have approximately the same energy, and are directed in the direction of the laser beam, with emission of the ions in a direction perpendicular to the laser beam.

12. The method according to claim 11, wherein the laser beam includes pulses of a few picoseconds in duration, with an interval between the pulses of a few picoseconds, and including focusing the laser beam on the pulsed jet of fluid, wherein the laser beam has an overcritical density.

13. The method according to claim 12, including filtering the beams of ions along a laser axis, using a movable filter.

14. The method according to claim 7, including focusing a laser pulse on the pulsed jet of fluid, with a density of the order of $10^{19}$ atoms/cm$^3$, thereby producing a divergent electron beam, spatially re-focusing the electron beam, and passing the re-focused electron beam through an undulator.

15. The method according to claim 14, including passing the electron beam that crossed the undulator through a which re-directs paths of electrons of the electron beam, thereby producing a beam exclusively of X-rays.

16. The method according to claim 14, wherein the undulator comprises a succession of magnets with alternating polarity so that electrons undulate upon passing through the undulator and radiate X-rays forwards, in the direction of the electron beam.

17. The method according to claim 16, wherein the magnets are periodically arranged and including varying the spectral range of the X-rays by varying period of the alternating magnets and intensity of magnetic fields produced by the magnets.

18. The method according to claim 11, including producing gamma rays by converting an electron beam, produced by interaction of a laser pulse with the pulsed jet of fluid having a density of the order of $10^{19}$ atoms/cm$^3$.

19. The method according to claim 18, including focusing the laser pulse with focusing optics having a focal length adapted to length of the jet so that the laser pulse is propagated in the jet of gas without filamentation.

20. The method according to claim 18, including impacting the electron beam on a mobile converter, thereby emission of gamma rays.

21. The method according to claim 20, including re-directing electrons of the electron beam in a bipolar magnet, thereby producing a beam of the gamma rays.

22. The method according to claim 11, including making the laser pulse incident on the pulsed jet of fluid with an overcritical density for wavelength of the laser pulse so that parasitic light does not cause breakdown of the plasma.

23. The method according to claim 11, including focusing the laser pulse in the jet of gas so that shorter wavelengths of the laser pulse are incident on the jet of gas before longer wavelengths, thereby recompressing the laser pulse over time.

* * * * *